United States Patent [19]

Uhl et al.

[11] 4,271,036

[45] Jun. 2, 1981

[54] COLORLESS FORMULATIONS OF OPTICAL BRIGHTENERS FROM THE SERIES OF BIS-TRIAZINYLAMINO-STILBENE-DISULFONIC ACID COMPOUNDS

[75] Inventors: Klaus Uhl, Bad Soden am Taunus; Hans Frischkorn, Hofheim am Taunus; Thomas Martini, Bad Soden am Taunus, all of Fed. Rep. of Germany

[73] Assignee: Hoechst Aktiengesellschaft, Fed. Rep. of Germany

[21] Appl. No.: 114,665

[22] Filed: Jan. 23, 1980

[30] Foreign Application Priority Data

Jan. 26, 1979 [DE] Fed. Rep. of Germany ....... 2902965

[51] Int. Cl.$^3$ ............................................. C09K 11/06
[52] U.S. Cl. ............................... 252/301.23; 542/435; 542/461
[58] Field of Search ............................... 542/461, 435; 252/301.23

[56] References Cited

U.S. PATENT DOCUMENTS

| | | | |
|---|---|---|---|
| 3,472,842 | 10/1969 | Hausermann et al. | 542/461 |
| 3,630,944 | 12/1971 | Ohkawa et al. | 252/301.23 |
| 3,941,778 | 3/1976 | Mueller et al. | 542/461 |
| 3,962,115 | 6/1976 | Clark et al. | 252/301.23 |
| 4,136,054 | 1/1979 | Petzold et al. | 252/301.21 |

FOREIGN PATENT DOCUMENTS 2633261  2/1977  Fed. Rep. of Germany ...... 252/301.23

*Primary Examiner*—Arthur P. Demers
*Attorney, Agent, or Firm*—Connolly and Hutz

[57] ABSTRACT

Colorless formulations of optical brighteners from the 4,4'-bis-triazinylamino-stilbene-disulfonic acid series, which are obtained by heating the brightener together with an oxyalkylate.

5 Claims, No Drawings

COLORLESS FORMULATIONS OF OPTICAL BRIGHTENERS FROM THE SERIES OF BIS-TRIAZINYLAMINO-STILBENE-DISULFONIC ACID COMPOUNDS

The detergent industry places great importance on the manufacture of pure white washing powders, and discolorations in the direction of green to yellow are unacceptable. However, numerous optical brighteners of the bis-triazinylstilbenedisulfonate series which are added to washing powders are initially obtained in a yellow-green to green modification in their manufacture, which cannot be employed as such since it imparts to the washing powder a color shade which deviates from white. These colored brightener modifications must thus first be converted into products which are white or have a slightly colored appearance.

In most cases, the conversion is effected by heating in an aqueous-alkaline medium and is accordingly troublesome and costly. It is now possible to employ the yellow-green to green modifications of cellulose brighteners of the triazinylstilbenedisulfonic acid series in the manufacture of washing powders in a manner such that the additional step of converting the modification into a white or only slightly colored product can be spared.

The invention relates to colorless formulations of optical brighteners of the formula

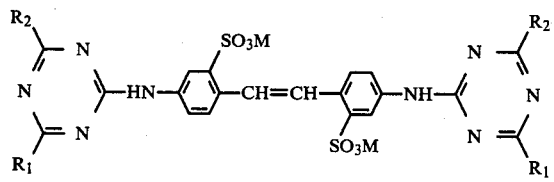

in which $R_1$ denotes $C_1$–$C_5$-alkoxy, anilino, halogenoanilino or morpholino, $R_2$ denotes $C_1$–$C_5$-alkoxy, morpholino or a group of the formula —$NR_3R_4$, $R_3$ denotes $C_2$–$C_4$-hydroxyalkyl, $R_4$ denotes $C_1$–$C_5$-alkyl or $C_2$–$C_4$-hydroxyalkyl, or $R_2$ denotes a group of the formula

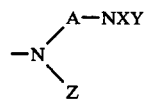

in which A denotes $C_2$–$C_6$-alkylene, X denotes a group of the formula —$COR_5$ or —$SO_2R_5$, $R_5$ denotes $C_1$–$C_5$-alkyl, $C_4$–$C_8$-cycloalkyl, phenyl or tolyl, Y denotes hydrogen or $C_1$–$C_5$-alkyl and Z denotes hydrogen, $C_1$–$C_5$-alkyl, $C_4$–$C_8$-cycloalkyl or a group of the formula —A—NXY, and M denotes an alkali metal atom or a hydrogen atom, which are obtained by heating a brightener of the above formula together with an oxalkylate. The two brighteners disodium 4,4'-bis[(4-anilino-6-morpholino-1,3,5-triazin-2-yl)amino]stilbene-2,2'-disulfonate and disodium 4,4'-bis[(4-anilino-6-(N-methyl-2-hydroxy-ethyl)-amino-1,3,5-triazin-2-yl)amino]stilbene-2,2'-disulfonate are preferred for this process.

Possible oxyalkylates in the context of the present invention are both polyethylene glycols and polypropylene glycols and the so-called non-ionic surface-active agents containing polyethylene glycol units or polypropylene glycol units. The polyethylene glycols and polypropylene glycols are products which have a degree of polymerization of up to 500, preferably of 1–40, and which contain either only polyethylene glycol units or polypropylene glycol units. In addition, possible oxyalkylates are also those which have the same degree of polymerization and which consist of the two types of groups in any desired ratio. Oxyethylation products or oxypropylation products of polyfunctional alcohols or amines, such as pentaerythritol or ethylenediamine, can also be used.

The non-ionic surface-active agents to be used are those products which are derived from a compound with one or more reactive hydrogen atoms, this hydrogen atom being replaced by a chain of oxyethyl units and/or oxypropyl units. A precise definition of the term nonionic surface-active agent can be found in the Textbook of Textile Auxiliaries by Chwala/Anger Verlag Chemie, Weinheim, New York, 1977, page 40.

The particularly interesting oxyalkylates can be represented by the general formula $$R-X(C_2H_4O)_y(C_3H_6O)_zH$$

in which R denotes $C_8$–$C_{20}$-alkyl or -alkenyl or mono-, di- or tri-$C_1$–$C_{12}$-alkylphenyl, X denotes an oxygen atom or a group of formula =N—$(C_2H_4O)_y(C_3H_6O)_zH$, —CONH— or —COO— and y and z denote numbers, the sum of which is 1 to 100, or R—X together denote the hydroxyl group and y and z denote numbers, the sum of which is 1 to 500, preferably 1 to 40. Of the non-ionic surface-active agents, those in which the radical R is derived from the following fatty acids are preferred: tallow fat acid, dec-9-en-1-oic acid, lauric acid, dodec-9-en-1-oic acid, myristic acid, tetradec-9-en-1-oic acid, palmitic acid, hexadec-9-en-1-oic acid, stearic acid, oleic acid, linoleic acid and linolenic acid. The alkyl group can, of course, also be branched, such as, for example, isotridecyl. Equally, R can also represent an alkylene group. It is understood that in all cases R can also be a mixture of different radicals under the above-mentioned meaning of R. Alkylphenyl groups which contain one or more alkyl groups with 1–20 C atoms, such as, for example, nonylphenyl or tributylphenyl, are also preferred. X is preferably an oxygen atom, that is to say oxyalkylated fatty alcohols and alkylphenols are possible preferred non-ionic surface-active agents.

The colorless formulation, according to the invention, of the abovementioned optical brighteners is prepared by a procedure in which the green-yellow to green modification of these brighteners is heated to about 30° to 180°, preferably 60° to 130° C., with one of the oxyalkylates described above, or mixtures thereof, for a short time, for example 1–20 minutes. The amount of optical brightener relative to the amount of oxyalkylates is about 0.5 to 40, preferably 1 to 20, % by weight. Depending on the nature of the oxyalkylate, on heating, either the dispersion present changes color from yellow-green to white or the brightener dissolves giving a colorless solution in order then, upon cooling, to crystallize out as colorless crystals together with the oxyalkylate or to form a colorless solution. In these cases, the formation of a colorless solution or dispersion can, however, be accelerated by adding small amounts of water. The amount of water added is between about 0.5 and 20% by weight, relative to the oxyalkylate. After adding the water, the change in color can take place immediately. It is also possible to heat the mixture of brightener and oxyalkylate via a procedure in which a liquid mixture of the two components is atomized by customary processes. In all cases, a mixture which contains the brightener in a colorless form is obtained and, even after standing for a relatively long period, re-discoloration of the cooled mixture is not to be observed.

The resulting colorless formulation of the optical brighteners of the above formula can be added directly, in the form of granules or in the form of a paste or liquid, to the slurry of washing powder. The form and also the concentration in which this brightener formulation is added to the slurry of washing powder depends on the particular industrial requirements of the manufacturer of the washing powder. The colorless formulation described above is added to the washing powder in an amount such that the washing powder has the usual content of brightener, which comprises about 0.1 to 0.3% by weight of the washing powder.

The colorless formulations, described above, of the optical brighteners have the advantage that the colorless form of the brightener is prepared with those products which as such already are, or can be, a constituent of washing powders, and that the product obtained in this conversion process can be added directly to the washing powder without further working up. Separate isolation of the colorless form of the brighteners, such as is necessary in the conventional processes, by heating in aqueous-alkaline solution, is thus dispensed with in the present case. Losses in yield such as occur in the conventional conversion of the modification are avoided here.

EXAMPLE 1

231 g of tallow fatty alcohol, oxyethylated with 25 ethylene oxide units, are heated to 80°–90° C. and 19 g of the green to green-yellow modification of the 92% pure powdered disodium salt of 4,4′-bis[(4-anilino-6-(N-methyl-N-2-hydroxy-ethyl)-amino)-1,3,5-triazin-2-yl) amino]stilbene-2,2′-disulfonic acid are introduced into the resulting colorless melt in the course of 15 minutes, whilst stirring thoroughly. The mixture is subsequently stirred at 80°–90° for 1.5 hours. A slightly turbid, slightly yellowish solution is formed, from which, after some time, the compound introduced precipitates again in the form of fine crystals, a whitish suspension being formed. For cooling, this suspension is poured onto a metal sheet, where it solidifies to a slightly pastel-colored to colorless, waxy mass. After flaking off, this mass can be processed, with the addition of dry ice, to give a colorless (white) powder.

EXAMPLE 2

88 g of tallow fatty alcohol, oxyethylated with 25 ethylene oxide units, are heated to 100°, with the addition of 4.5 g of water, and 7.6 g of the 92% pure disodium salt of 4,4′-bis-[(4-anilino-6-(N-methyl-N-2-hydroxy-ethyl)-amino)-1,3,5-triazin-2-yl)amino]stilbene-2,2′-disulfonic acid in the green to yellow-green modification are introduced into the resulting colorless melt in the course of 10 minutes, whilst stirring thoroughly. The mixture is subsequently stirred for a further 2 hours at 100° and a homogeneous slightly turbid solution is formed. This is then poured onto a metal sheet to cool. A slightly pastel-colored, waxy mass is obtained, which can be flaked off and ground, with the addition of dry ice, to give a colorless powder.

EXAMPLE 3

(a) 0.3 g of the brightener of the formula

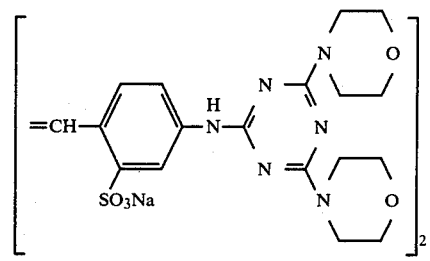

(green to green-yellow modification) are added to 3 g of the oxyethylation product of tallow fatty alcohol with 25 ethylene oxide units, the components are mixed intensively and the mixture is heated to 100°–130°, whilst stirring. 0.2–0.3 g of $H_2O$ are added to the melt, whereupon the color changes to a pastel color. This color shade is retained, even after cooling.

The same experiment is carried out with in each case the green to green-yellow modification of the following stilbene brighteners:

(b)

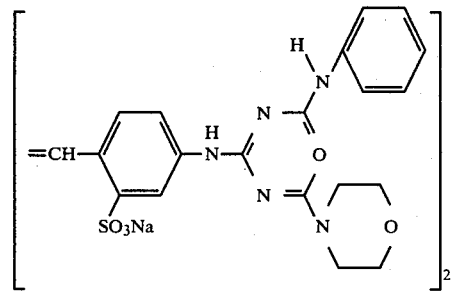

color change to white.

(c)

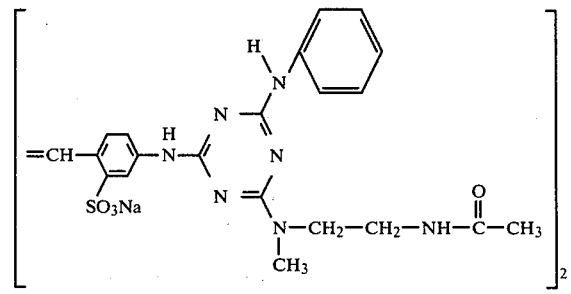

color change to white (d)

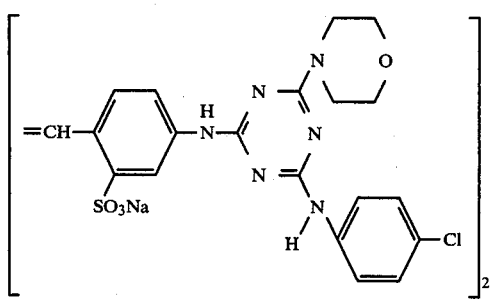

color change to white
(e)

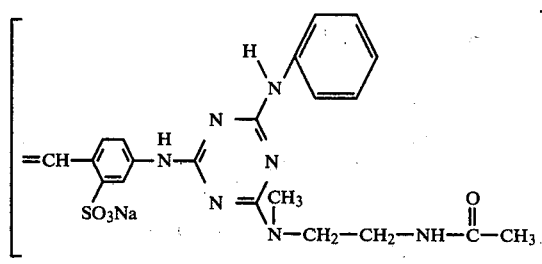

color change from green to slightly yellow

EXAMPLE 4

In each case 3 g of the non-ionic surface-active agent indicated and 0.3 g of the green to yellow-green α-modification of the brightener

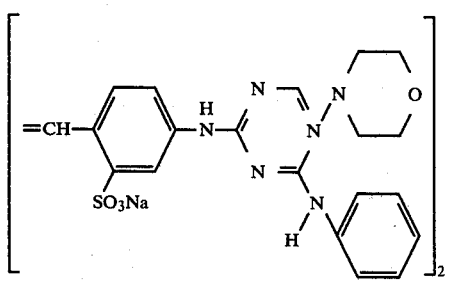

are heated to 100°–120° in a glass beaker. 0.3 g of $H_2O$ is added to the green molten suspension, whilst stirring. The resulting color shade indicated does not change when the mixture is left to stand and cools.

(a) Isotridecyl alcohol—oxyethylated with 8 ethylene oxide units
formation of a white dispersion
(b) Isotridecyl alcohol—oxyethylated with 15 ethylene oxide units
formation of a colorless solution which, on standing and cooling, becomes turbid like a dispersion and remains pure white.
(c) Oleyl alcohol—oxyethylated with 12 ethylene oxide units
formation of a white paste
(d) Coconut alcohol—oxyethylated with 5 ethylene oxide units
formation of a white dispersion
(e) A mixture of 10% of nonyl alcohol—oxyethylated with 5 ethylene oxide units, 25% of decyl alcohol—oxyethylated with 5 ethylene oxide units, 15% of undecyl alcohol—oxyethylated with 5 ethylene oxide units, 10% of dodecyl alcohol—oxyethylated with 5 ethylene oxide units, 12.5% of tridecyl alcohol—oxyethylated with 5 ethylene oxide units, 18.5% of $C_{14}$-alcohol—oxyethylated with 5 ethylene oxide units, and 9% of $C_{15}$-alcohol—oxyethylated with 5 ethylene oxide units
formation of a pastel-colored, waxy mass.
(f) Stearyl alcohol—oxyethylated with 2 ethylene oxide units
formation of a white dispersion
(g) Stearyl alcohol—oxyethylated with 20 ethylene oxide units
formation of a colorless solution which crystallizes to give white crystals on standing.
(h) Tallow fatty alcohol—oxyethylated with 25 ethylene oxide units
formation of a slightly yellowish solution which solidifies as a white substance on cooling. The resulting test mass gives, when comminuted, a virtually white powder.
(i) Nonylphenol—oxyethylated with 25 ethylene oxide units
formation of a pastel-colored, waxy mass
(j) Tributylphenol—oxyethylated with 10 ethylene oxide units
formation of a white dispersion.

EXAMPLE 5

In a procedure as in Example 3, a polyethylene glycol with a degree of polymerization of about 80–100 is employed instead of the surface-active agent. A colorless solution is initially obtained, and after cooling white crystals are obtained.

The same is true for a polyethylene glycol with a degree of polymerization of 200–250.

EXAMPLE 6

In a procedure as in Example 3, the green to yellow-green modification of the brightener is added to a copolymer of ethylene oxide and propylene oxide with an ethylene oxide content of 80% and a propylene oxide content of 20% and a molecular weight of between 6,600 and 9,300, and the mixture is heated to 90°–120° C. for 3–4 minutes. After adding water, a white to pastel-colored suspension is initially formed. After standing at room temperature for 48 hours, a colorless solution is formed from the suspension.

EXAMPLE 7

In a procedure as in Example 3, a product prepared by adding ethylene oxide and propylene oxide onto ethylenediamine, 30 ethylene oxide units and 60 propylene oxide units being added on per ethylenediamine unit, is heated with the brightener, and $H_2O$ is added. The yellow-green suspension is thereby converted into a colorless solution.

If a derivative of pentaerythritol etherified with ethylene oxide and propylene oxide in the ratio 3:1 is used instead of the ethylenediamine derivative, a white dispersion is obtained.

EXAMPLE 8

800 g of the brightener/surface-active agent mixture prepared according to Example 1, with a brightener content of 7.5%, is added at 80° C. to a washing powder slurry consisting of 14,000 g of H₂O, 350 g of tylose, 280 g of NaHCO₃, 3,600 g of a 60% strength sec.-alkanesulfonate, 4,250 g of waterglass of 40° Bé strength, 12,100 g of Na-triphosphate and 310 g of Na₂SO₄ and the mixture is stirred at this temperature for 30 minutes. The slurry is sprayed with a hot-air counter-current spray-drying unit with an air inlet temperature of 95° C., through a one-material nozzle (φ 3.5 mm) and under a pump pressure corresponding to a gauge pressure of 70 bars. The powder thus obtained is pure white and does not become green even under extreme moisture conditions and extreme temperatures (water content 30–35%, 45°–50° C.). A comparison experiment in which the non-ionic surface-active agent and yellow-green modification of the brightener were added separately gave a greenish-colored washing powder.

EXAMPLE 9

A solution of 2.5 g of water and 0.6 g of Na₂CO₃ is added to 44 g of a tallow fatty alcohol, oxyethylated with 25 ethylene oxide units, and the mixture is heated to 90° C., whereupon a turbid melt forms. 3.5 g of the green to green-yellow modification of the compound 4,4′-bis[(4-anilino-6-(N-methyl-2-hydroxy-ethyl)amino-1,3,5-triazin-2-yl)amino]stilbene-2,2′-disulfonic acid are added and the mixture is warmed to 90°–110° C. for 1½ hours and a further 5 ml of H₂O are then added. A slightly yellowish turbid solution is obtained which solidifies when cold and, when flaked and cooled with dry-ice, can be ground. The resulting powder has only a slightly yellowish sheen and gives, when added to a slurry of washing powder, a colorless slurry and also a colorless sprayed powder.

EXAMPLE 10

4.2 g of a pastel caramel-colored 20 percent strength formulation, prepared according to Example 2, of the yellow-green modification of the brightener disodium 4,4′-bis[(4-anilino-6-(N-methyl-N-2-hydroxyethyl)amino-1,3,5-triazin-2-yl)amino]stilbene-2,2′-disulfonate (92 percent pure) in a tallow fatty alcohol oxyethylated with 11 ethylene oxide units are added to 30 g of a sec.-alkanesulfonate (60 percent strength) with C chain length spread of C₁₃ to C₁₈, whilst stirring. The mixture assumes a slight yellow shade and its color does not change even after prolonged storage. Furthermore, simultaneously using the oxyethylated fatty alcohol reduces the viscosity.

In contrast, if 0.8 g of the colorless or green-yellow modification of the abovementioned brightener is added to the sec.-alkanesulfonate, intensely green-colored alkanesulfonate formulations are obtained immediately in the latter case and after standing for 2 days when the colorless modification is used. When added to a slurry of washing powder, these green alkanesulfonate formulations discolor the sprayed washing powder.

We claim:

1. Colorless formulation of optical brighteners of the formula

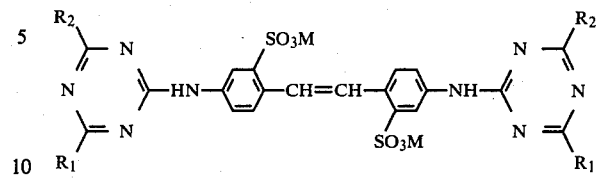

in which $R_1$ denotes $C_1$–$C_5$-alkoxy, anilino, halogenoanilino or morpholino, $R_2$ denotes $C_1$–$C_5$-alkoxy, morpholino or a group of the formula —NR₃R₄, $R_3$ denotes $C_2$–$C_4$-hydroxyalkyl, $R_4$ denotes $C_1$–$C_5$-alkyl or $C_2$–$C_4$-hydroxyalkyl, or $R_2$ denotes a group of the formula

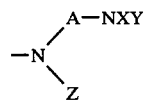

in which A denotes $C_2$–$C_6$-alkylene, X denotes a group of the formula —COR₅ or —SO₂R₅, R₅ denotes $C_1$–$C_5$-alkyl, $C_4$–$C_8$-cycloalkyl, phenyl, or tolyl, Y denotes hydrogen or $C_1$–$C_5$-alkyl and Z denotes hydrogen, $C_1$–$C_5$-alkyl, $C_4$–$C_8$-cycloalkyl or a group of the formula —A—NXY, and M denotes an alkali metal atom or hydrogen atom, which are obtainable by heating a brightener of the above formula together with an oxyalkylate of the formula

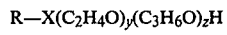

in which R denotes $C_8$–$C_{20}$-alkyl or -alkenyl or mono-, di- or tri-$C_1$–$C_{12}$-alkylphenyl, X denotes an oxygen atom or a group of the formula =N—(C₂H₄O)ᵧ(C₃H₆O)ᵤH, —CONH— or —COO— and y and z denote numbers, the sum of which is 1 to 100, or R—X together denote the hydroxyl group and y and z denote numbers, the sum of which is 1 to 500, preferably 1 to 40.

2. Formulations as claimed in claim 1, which are obtainable by heating the oxyalkylate with 0.5 to 40% by weight of optical brightener, relative to the oxyalkylate.

3. Formulations as claimed in claim 1, which are obtainable by heating the optical brightener and the oxyalkylate to 30° to 180° C.

4. Formulations as claimed in claim 1, which are obtainable by heating the brightener and the oxyalkylate together with 0.5 to 20% by weight of water, relative to the oxyalkylate.

5. Formulations as claimed in claim 1, which contain, as the brightener, disodium 4,4′-bis[(4-anilino-6-morpholino-1,3,5-triazin-2-yl)amino]stilbene-2,2′-disulfonate or disodium 4,4′-bis[(4-anilino-6-(N-methyl-2-hydroxyethyl)-amino-1,3,5-triazin-2-yl)amino]stilbene-2,2′-disulfonate.

* * * * *